(12) United States Patent
Schwartzbard et al.

(10) Patent No.: US 11,232,555 B2
(45) Date of Patent: Jan. 25, 2022

(54) SYSTEMS AND METHODS FOR AUTOMATED ANALYSIS OF MEDICAL IMAGES

(71) Applicant: NEC Corporation Of America, Herzlia (IL)

(72) Inventors: Yael Schwartzbard, Tel-Aviv (IL); Yaacov Hoch, Ramat-Gan (IL); Tsvi Lev, Tel-Aviv (IL)

(73) Assignee: NEC Corporation Of America, Herzlia (IL)

( * ) Notice: Subject to any disclaimer, the term of this patent is extended or adjusted under 35 U.S.C. 154(b) by 406 days.

(21) Appl. No.: 16/247,801

(22) Filed: Jan. 15, 2019

(65) Prior Publication Data

US 2020/0226746 A1    Jul. 16, 2020

(51) Int. Cl.
| | | |
|---|---|---|
| *G06K 9/00* | (2006.01) | |
| *G06T 7/00* | (2017.01) | |
| *A61B 6/00* | (2006.01) | |
| *G06T 7/70* | (2017.01) | |
| *G06K 9/62* | (2006.01) | |
| *G06T 7/11* | (2017.01) | |
| *G06T 3/40* | (2006.01) | |
| *G06T 3/60* | (2006.01) | |
| *A61B 6/03* | (2006.01) | |

(52) U.S. Cl.
CPC ............ *G06T 7/0012* (2013.01); *A61B 6/032* (2013.01); *A61B 6/5217* (2013.01); *G06K 9/6256* (2013.01); *G06K 9/6277* (2013.01); *G06T 3/40* (2013.01); *G06T 3/60* (2013.01); *G06T 7/11* (2017.01); *G06T 7/70* (2017.01); *G06K 2209/05* (2013.01); *G06T 2207/10081* (2013.01); *G06T 2207/10088* (2013.01); *G06T 2207/10104* (2013.01); *G06T 2207/10132* (2013.01); *G06T 2207/20076* (2013.01); *G06T 2207/20081* (2013.01)

(58) Field of Classification Search
None
See application file for complete search history.

(56) References Cited

U.S. PATENT DOCUMENTS

| | | | | |
|---|---|---|---|---|
| 2018/0271460 A1* | 9/2018 | Geiger | ............... | G01R 33/4814 |
| 2018/0342060 A1* | 11/2018 | Yao | ........................ | A61B 8/468 |
| 2020/0160122 A1* | 5/2020 | Lints | ...................... | A61B 6/563 |
| 2021/0004960 A1* | 1/2021 | Groth | ........................ | G06T 7/10 |

\* cited by examiner

*Primary Examiner* — Sean M Conner

(57) ABSTRACT

There is provided a computed implemented method of automatically generating an adapted presentation of at least one candidate anomalous object detected from anatomical imaging data of a target individual, comprising: providing anatomical imaging data of the target individual acquired by an anatomical imaging device, analyzing the anatomical imaging data by a detection classifier for detecting at least one candidate anomalous object of the anatomical imaging data and computed associated location thereof, computing, by a presentation parameter classifier, at least one presentation parameter for adapting a presentation of a sub-set of the anatomical imaging data including the at least one candidate anomalous object according to at least the location of the candidate anomalous object, and generating according to the at least one presentation parameter, an adapted presentation of the sub-set of the anatomical imaging data including the at least one candidate anomalous object.

25 Claims, 8 Drawing Sheets

502 3D Thresholded CT scan (detected by AI)

504 Segmented single object from 3D CT Scan (rotated and segmented by AI)

506 Skeletonized single object from 3D CT Scan

← 706  A nodule adjacent to a lung wall viewed from the default CT orientation (supine position CT)

← 708  Same area rotated by the AI supplied parameters to optimally show the nodule and lung wall

SYSTEMS AND METHODS FOR AUTOMATED ANALYSIS OF MEDICAL IMAGES

FIELD AND BACKGROUND OF THE INVENTION

The present invention, in some embodiments thereof, relates to medical imaging analysis and, more specifically, but not exclusively, to systems and methods for automated analysis of medical images.

Medical images, such as 2D and/or 3D images created by devices such as CT, MRI, X-Ray, and PET, include a large amount of information for inspection, for example, a CT scan may include dozens of slices. Manual inspection of such images to detect anomalies (e.g., tumors which may be cancerous) takes a significant amount of time. Processes for automatically analyzing the medical images to detect anomalies, and reduce the amount of time to be spent by radiologists (or other healthcare professionals trained to interpret medical images) are sought.

SUMMARY OF THE INVENTION

According to a first aspect, a computed implemented method of automatically generating an adapted presentation of at least one candidate anomalous object detected from anatomical imaging data of a target individual, comprises: providing anatomical imaging data of the target individual acquired by an anatomical imaging device, analyzing the anatomical imaging data by a detection classifier for detecting at least one candidate anomalous object of the anatomical imaging data and computed associated location thereof, computing, by a presentation parameter classifier, at least one presentation parameter for adapting a presentation of a sub-set of the anatomical imaging data including the at least one candidate anomalous object according to at least the location of the candidate anomalous object, and generating according to the at least one presentation parameter, an adapted presentation of the sub-set of the anatomical imaging data including the at least one candidate anomalous object.

According to a second aspect, a computer implemented method of training a presentation parameter classifier for computing at least one presentation parameter, comprises: providing respective training anatomical imaging data for each of a plurality of sample individuals, computing by a detection classifier, for each respective training anatomical imaging data, an indication of at least one training candidate anomalous object and associated location thereof, providing, for each respective training anatomical imaging data, at least one training presentation parameter for adapting a presentation of a sub-set of the anatomical imaging data including the at least one candidate anomalous object according to at least the location of the candidate anomalous object, and training the presentation parameter classifier for computing at least one presentation parameter for a target anatomical imaging data of a target individual when an indication of at least one candidate anomalous object and associated location thereof computed for the target anatomical imaging data is provided as input into the presentation parameter classifier.

According to a third aspect, a system for automatically generating an adapted presentation of at least one candidate anomalous object detected from anatomical imaging data of a target individual, comprises: at least one hardware processor, and a non-transitory memory having stored thereon a code for execution by the at least one hardware processor, the code comprising instructions for: obtaining anatomical imaging data of the target individual acquired by an anatomical imaging device, analyzing the anatomical imaging data by a detection classifier for detecting at least one candidate anomalous object of the anatomical imaging data and computed associated location thereof, computing, by a presentation parameter classifier, at least one presentation parameter for adapting a presentation of a sub-set of the anatomical imaging data including the at least one candidate anomalous object according to at least the location of the candidate anomalous object, and generating according to the at least one presentation parameter, an adapted presentation of the sub-set of the anatomical imaging data including the at least one candidate anomalous object.

In a further implementation form of the first, second, and third aspects, the presentation parameter classifier further computes the at least one presentation parameter according to at least one neighboring anatomical feature indicative of anatomical features located in proximity to the candidate anomalous object.

In a further implementation form of the first, second, and third aspects, the at least one anatomical feature indicative of neighboring anatomical features located in proximity to the candidate anomalous objects is selected from the group consisting of: organ within which the respective candidate anomalous object is located, tissue type within which the respective candidate anomalous object is located, and normal predefined anatomical landmark in proximity to the respective candidate anomalous object.

In a further implementation form of the first, second, and third aspects, the at least one anatomical feature indicative of neighboring anatomical features located in proximity to each respective candidate anomalous objects is computed by a segmentation classifier that segments a patch of the anatomical imaging data that includes the respective candidate anomalous object.

In a further implementation form of the first, second, and third aspects, the at least one presentation parameter comprises dimensions of the sub-set of the anatomical imaging data including the at least one candidate anomalous object, the dimensions selected according to the at least one neighboring anatomical feature.

In a further implementation form of the first, second, and third aspects, the dimensions are selected for including the external boundaries of the at least one neighboring anatomical feature and at least a portion of anatomical features located in proximity to the at least one candidate anomalous object.

In a further implementation form of the first, second, and third aspects, the at least one presentation parameter comprises a scale factor for enlarging the sub-set of the anatomical imaging data including the at least one candidate anomalous object, the scale factor is selected according to the at least one neighboring anatomical feature.

In a further implementation form of the first, second, and third aspects, the scale factor is inversely correlated to a distance to the at least one neighboring anatomical feature, wherein a relatively larger scale factor is selected for a relatively smaller distance.

In a further implementation form of the first, second, and third aspects, the at least one presentation parameter comprises a rotation angle of the sub-set of the anatomical imaging data including the at least one candidate anomalous object to at least one viewing angle selected according to the at least one neighboring anatomical feature.

In a further implementation form of the first, second, and third aspects, the at least one presentation parameter comprises a value of a CT window selected according to the at least one neighboring anatomical feature.

In a further implementation form of the first, second, and third aspects, the at least one presentation parameter is selected for improving visual inspection of the at least one candidate anomalous object relative to neighboring anatomical features, for classification of the at least one candidate anomalous object as an anomaly.

In a further implementation form of the first, second, and third aspects, the candidate anomalous objects are associated with a probability value indicative of estimate likelihood of the respective candidate anomalous object denoting an actual anomaly, and further comprising selecting a subset of the candidate anomalous objects having probability values within a range denoting statistical uncertainty for automatically designating the candidate anomalous objects as actual anomalies, wherein the at least one presentation parameter is computed for each member of the selected subset of the candidate anomalous objects, and the adapted presentation is generated for each member of the selected subset of candidate anomalous objects according to corresponding at least one presentation parameter.

In a further implementation form of the first, second, and third aspects, the range includes candidate anomalous objects having probability values above a lower threshold denoting statistically insignificant likelihood of the respective candidate anomalous object being designated as an actual anomaly, and below an upper threshold denoting statistically significant likelihood of the respective candidate anomalous object being designated as an actual anomaly.

In a further implementation form of the first, second, and third aspects, the lower threshold is selected from the range 50-70%, and the upper threshold is selected from the range 90-100%.

In a further implementation form of the first, second, and third aspects, a unique set of presentation parameters is computed independently for each respective candidate anomalous object according to respective corresponding sub-set of the anatomical imaging data, and wherein a unique adapted presentation is computed independent for each respective candidate anomalous object according to respective corresponding unique set of presentation parameters.

In a further implementation form of the first, second, and third aspects, the viewing angle is selected to at least one of: remove or reduce obstructions from the anatomical features located in proximity to the candidate anomalous object, position anatomical features located in proximity to the candidate anomalous object at a predefined reference orientation, and depict selected anatomical features of the at least one candidate anomalous object.

In a further implementation form of the first, second, and third aspects, the at least one presentation parameter comprises a plurality of rotation angles, and the adapted presentation comprises a video created by rotation of the sub-set of the anatomical imaging according to the plurality of rotation angles.

In a further implementation form of the first, second, and third aspects, the method further comprises and/or the system further comprises code instructions for computing a segmentation of the at least one candidate anomalous object, and wherein the at least one presentation parameter is selected according to the segmentation of the at least one candidate anomalous object.

In a further implementation form of the first, second, and third aspects, the at least one presentation parameter is selected from the group consisting of: removing neighboring anatomical features located externally to the boundaries of the segmented at least one candidate anomalous object, coloring the segmented at least one candidate anomalous object with at least one color, highlighting the segmented at least one candidate anomalous object, extracting the segmented at least one candidate anomalous object, and skeletonization of the segmented at least one candidate anomalous object.

In a further implementation form of the first, second, and third aspects, the method further comprises and/or the system further comprises code instructions for obtaining from a reference dataset, at least one reference anatomical imaging data including at least one reference anomalous object correlated to the detected at least one candidate anomalous object, wherein the at least one presentation parameter is selected according to the at least one reference anatomical imaging data, and wherein the adapted presentation of the sub-set of the anatomical imaging data is presented in association with a presentation of the at least one reference anatomical image.

In a further implementation form of the first, second, and third aspects, the at least one presentation parameter of the sub-set of the anatomical imaging data including the at least one candidate anomalous object are obtained according to corresponding stored presentation parameters associated with the at least one reference anatomical imaging data.

In a further implementation form of the first, second, and third aspects, the presentation of the at least one reference anatomical image is generated using the at least one presentation parameter computed for of the sub-set of the anatomical imaging data including the at least one candidate anomalous object.

In a further implementation form of the first, second, and third aspects, the imaging data comprises 3D imaging data acquired by a 3D imaging device.

In a further implementation form of the first, second, and third aspects, the 3D imaging device is selected from the group consisting of: computed tomography (CT), magnetic resonance imaging (MRI), positron emission tomography (PET), and ultrasound (US).

In a further implementation form of the second aspect, the method further comprises providing at least one neighboring anatomical feature indicative of anatomical features located in proximity to the candidate anomalous object, and training the presentation parameter classifier for computing at least one presentation parameter when an indication of the at least one neighboring anatomical feature indicative of anatomical features located in proximity to the candidate anomalous object is further provided as input into the presentation parameter classifier.

In a further implementation form of the third aspect, the system further comprises code instructions for: obtaining respective training anatomical imaging data for each of a plurality of sample individuals, computing by a detection classifier, for each respective training anatomical imaging data, an indication of at least one training candidate anomalous object and associated location thereof, obtaining, for each respective training anatomical imaging data, at least one training presentation parameter for adapting a presentation of a sub-set of the anatomical imaging data including the at least one candidate anomalous object according to at least the location of the candidate anomalous object, and training the presentation parameter classifier for computing at least one presentation parameter for a target anatomical imaging data of a target individual when an indication of at least one candidate anomalous object and associated location thereof computed for the target anatomical imaging data is provided as input into the presentation parameter classifier.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
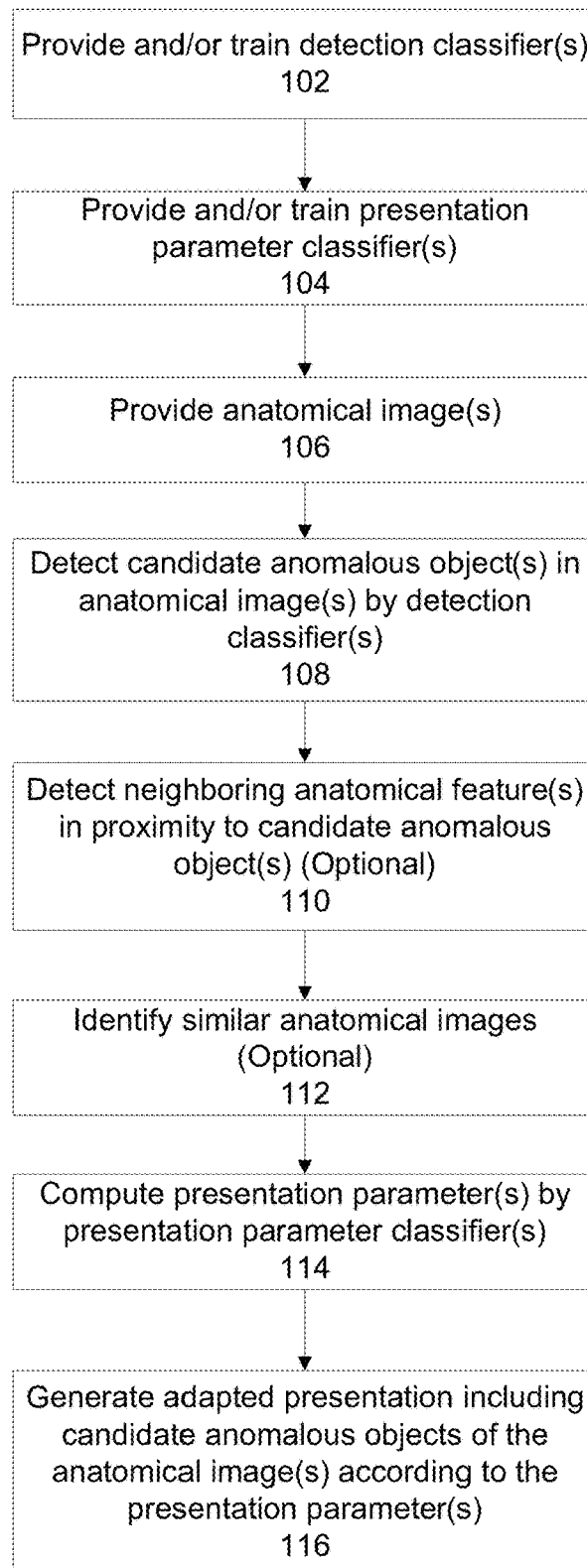
FIG. 1 is a flowchart of a method of automatically generating an adapted presentation of candidate anomalous object(s) automatically detected from anatomical imaging data of a target individual, in accordance with some embodiments of the present invention.

The present invention, in some embodiments thereof, relates to medical imaging analysis and, more specifically, but not exclusively, to systems and methods for automated analysis of medical images.

As used herein, the term anomalous object (or candidate anomalous object) may refer to a representation of tangible anatomical tissue that is physically located within the target individual, and/or other physical substance physically located within the target individual, when presented within the captured anatomical image. The candidate anomalous object may be an abnormal object not normally present within the target individual which may represent malignancy, for example, a solitary pulmonary nodule. In another example, the candidate anomalous object may be an abnormal physical substance not normally present within the target individual, which may hint towards an underlying clinical problem, for example, the presence of air and/or other body fluids in locations where such air and/or other body fluid is not normally found. It is noted that the anomalous object is indicative of actual tissue and/or cells and/or abnormal physical substance, rather than a sign and/or diagnosis.

As used herein, the terms anatomical image and anatomical imaging data may sometimes be interchanged.

An aspect of some embodiments of the present invention relates to systems, methods, an apparatus, and/or code instructions (e.g., stored on a data storage device, executable by one or more hardware processors) for automatically generating an adapted presentation of one or more candidate anomalous objects automatically detected from anatomical imaging data of a target individual. The candidate anomalous object(s) and associated location are automatically detected by a detection classifier that analyzes anatomical images. A presentation parameter classifier computes one or more presentation parameters for adapting a presentation of a portion (also referred to herein as sub-set) of the anatomical image that includes at least one or more candidate anomalous objects. The presentation parameter(s) are selected for improving visual inspection of the candidate anomalous object(s), optionally relative to neighboring anatomical features. The portion is selected according to the computed location of the candidate anomalous object(s), and optionally includes one or more neighboring anatomical features of anatomical features location in proximity to the candidate anomalous object(s). An adapted presentation of the portion the anatomical imaging data is automatically generated based on the computed presentation parameters, for example, a 2D image presented on a display, a video of a 3D image presented on a display (e.g., rotation of the image through different viewing angles), and/or an image presented on a virtual reality display. A user (e.g., radiologist) viewing the adapted presentation may classify (e.g., assign a diagnosis) to each candidate anomalous object, for example, whether the respective candidate anomalous object denotes an actual abnormality or not (i.e., the automated detection process incorrectly identified the candidate anomalous object).

At least one implementations of the systems, apparatus, methods, and/or code instructions described herein address the technical problem of improving the detection rate for identifying anomalous objects in imaging data, for example, identifying detection of solitary pulmonary nodules in low dose CT imaging for lung cancer screening. In particular, reducing the false positive and/or false negative detection rate of anomalies. Automated processes (e.g., machine learning, deep learning neural networks) for detecting anomalous objects in imaging data have an inherent tradeoff between their sensitivity (i.e., ability to detect all real anomalies) and their level of specificity and/or false positives or false alarms (i.e., detecting normal tissue areas as an anomaly). For example, on cross section, a nodule may look like a blood vessel. Inspection of a 3D sample of imaging data is required to be able to discern the nodule (which is about round in shape) from a blood vessel (which extends in length in space). In another example, inspection of pulmonary nodules next to the wall of the chest may be required to determine whether the finding is a pulmonary nodule (i.e., not connected to the chest wall), or not a pulmonary nodule (i.e., connected to the chest wall). Moreover, the different types of pulmonary nodules may make their automated detection more difficult and require visual inspection, for example, solid, semi-solid, and ground glass. In practice, to avoid missing anomalies (e.g., cancerous tumors), a Radiologist that completely relies on an automated process to detect candidate regions, is required to manually inspect all of the detected regions, which may include a significantly large number of regions that are falsely detected as anomalies (but are in fact normal tissue).

For example, in Lung CT radiology, current state of the art Deep Learning results may detect >95% of all actual pulmonary nodules (i.e., anomalies). However, detection of the pulmonary nodules is at the cost of the deep learning methods also generating a large number (e.g., several dozen) false alarms, which are normal tissue incorrectly identified as pulmonary nodules. When the number of falsely detected areas is too large, the utility and value of the automated detection process is questionable. In such cases the radiologist might be better off just inspecting the whole image visually without automated detection.

For example, in CT radiology, the total inspection time allocated to a chest CT might be 10-15 minutes. Of the total time, just a few minutes are allocated to nodule detection and inspection. In such a case, if the inspection of each false alarm (out of dozens) takes 30 seconds, the process is non-productive, since it would take longer to inspect the CT scan that was analyzed by the automated detection process rather than visually inspecting the CT scan without using the automated detection process.

At least one implementations of the systems, apparatus, methods, and/or code instructions described herein provide a technical solution to the technical problem of generating an adapted presentation of the automatically detected anomalous objects. The adapted presentation is designed to be optimized for visual inspection by the radiologist. The optimized adapted presentation is designed to reduce the time for visual inspection of the anomalous objects to determine if each object is a possible clinically significant finding or not, for example, determine whether the anomalous object is a solitary pulmonary nodule or not, such as in 5 seconds or less. The ability to rapidly visually inspect the automatically detected abnormalities increases efficiency and/or accuracy of analyzing the imaging data to detect actual anomalous objects in comparison to standard manual methods and/or to using exiting detection methods combined with visual inspection methods.

At least some implementations of the systems, apparatus, methods, and/or code instructions described herein improve the medical field of analyzing medical images to detect anomalous objects, by improving the detection rate for identifying anomalous objects in imaging data, for example, improving the medical field of accurately detecting solitary pulmonary nodules in low dose CT imaging for lung cancer screening. As discussed herein, using standard methods, which are entirely manual or semi-manual (where a large number of candidate anomalous objects including a large number of false positive and/or false negative findings), a user (e.g., radiologist) manually inspects each candidate anomalous object and/or inspects the entire image to determine whether the candidate anomalous object is an actual anomaly or not. It is noted that in many cases, such as CT scans which may include a gigabyte of pixel data, a large number of slices are generated. Such manual analysis is subjective, based on the individual radiologist looking at the anatomical images. Two different radiologists looking at the same candidate anomaly, or same CT image, may provide different opinions regarding actual anomalous findings. In another example, different radiologists may arrive at different results due to different applied processing of the anatomical images, for example, using different CT windows to view the images. Radiologists that are not familiar and/or experienced with such settings for optimal viewing of images may arrive at incorrect interpretation of the images.

The automated generation of adapted presentation of candidate anomalous objects in anatomical images by at least some systems, methods, apparatus, and/or code instructions described herein is not based on a simple coding of an existing manual process onto a computer. Rather, at least some systems, methods, apparatus, and/or code instructions described herein turn a subjective method into an objective, reproducible method. Inventors developed new steps that did not previously exist in the manual process, and do have not counterparts in the manual process, namely, training and/or use of the detection classifier and/or the presentation parameter classifier, generation of instructions for adaption of the anatomical imaging data according to the detected candidate anomalous objects. At least some implementations of the systems, apparatus, methods, and/or code instructions described herein provide objective, reproducible visual object identification results, which are not available using standard manual processes.

At least some implementations of the systems, apparatus, methods, and/or code instructions described herein address the technical problem of automatically and accurately detecting anomalous objects in anatomical medical images, for medical therapy of the patient. Incorrectly determined anomalous objects (i.e., identifying an anomalous object where none actually exists) may subject the patient to unnecessary additional procedures to obtain a sample of the anomalous object for further diagnosis and/or unnecessary removal of the anomalous object, for example, biopsy, surgery, other invasive procedure to obtain a sample, and/or imaging associated with risks (e.g., due to radiation and/or contrast administration). On the flip side, missing an existing anomalous object may be detrimental to the patient, for example, failure to remove an early stage cancer (which may result in a full cure) may allow the cancer to grow and metastasize to the point where a cure is unlikely. Therefore, accurate image based identification of anomalous objects is clinically important, but technically challenging.

It is technically challenging to design and train a statistical classifier that detects anomalous objects in anatomical medical images, in terms of accuracy of detection (i.e., high sensitivity, low false positive and/or false negative rate) and/or in terms of computational efficiency of a computing device that trains and/or executes the classifiers. For example, the training dataset used to train the classifier may be very large, requiring large memory resources to store the images and/or sufficiency processing resources to process the images. For example, each 3D anatomical image may be on the order of gigabytes, and dozens, hundred, or thousands of images are required for training. Each patch inputted into the classifier (e.g., convolutional neural network (CNN)) may be large on the order of 32K (e.g., 32×32×32) or more. Moreover, designing and/or training the classifier to accurately perform detection may be difficult, for example, due to lack of sufficiently available number of labeled anatomical images for training the classifiers, even when labeled images are available the labels may be incorrect and/or ambiguous, introducing errors into the training process, and/or mechanical turks cannot be used.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server.

In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, which is a flowchart of a method of automatically generating an adapted presentation of candidate anomalous object(s) automatically detected from anatomical imaging data of a target individual, in accordance with some embodiments of the present invention.

Figure 2:
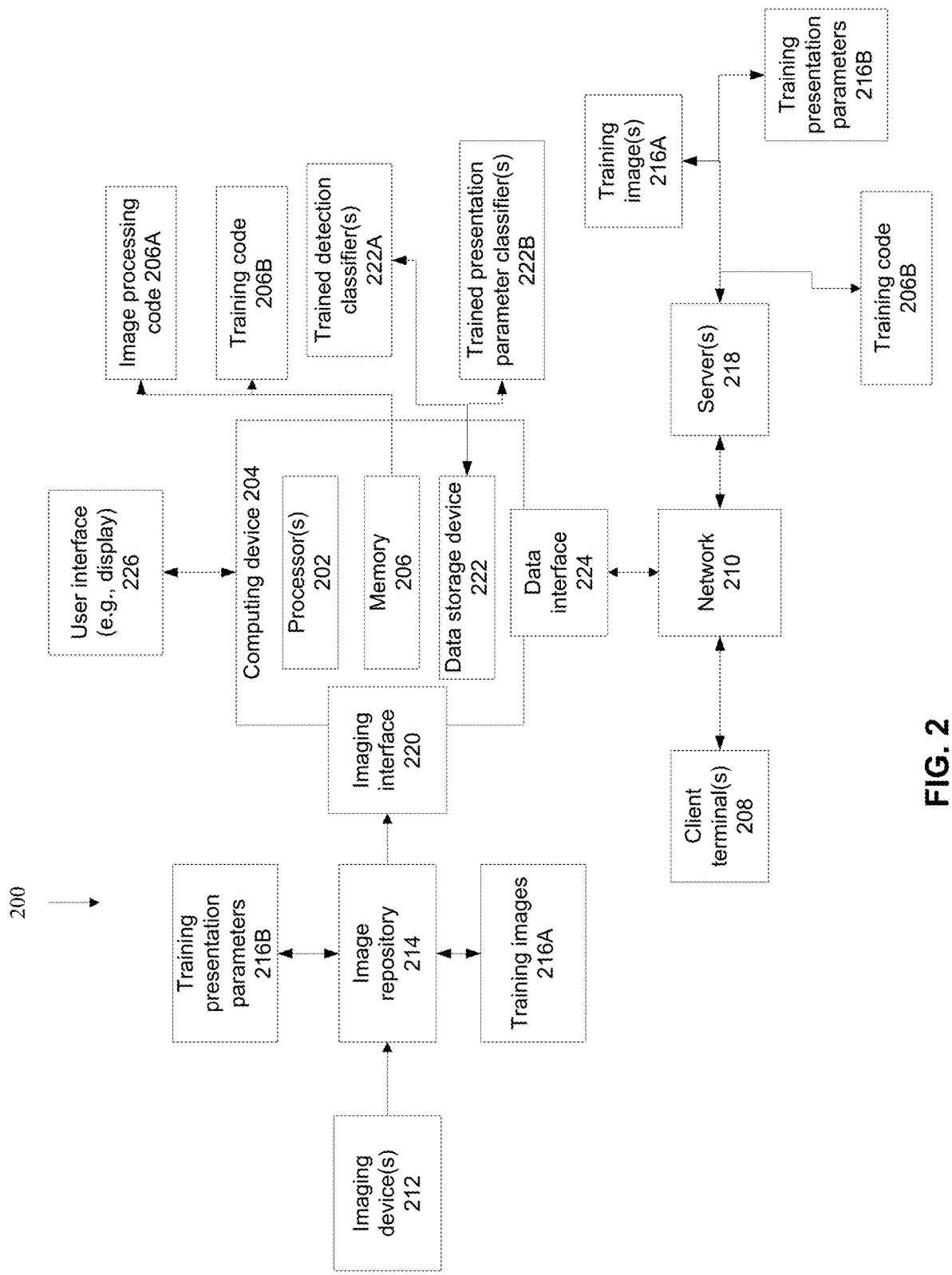
FIG. 2 is a block diagram of components of a system for automatically generating an adapted presentation of candidate anomalous object(s) automatically detected from anatomical imaging data of a target individual, in accordance with some embodiments of the present invention.
Figure 3:
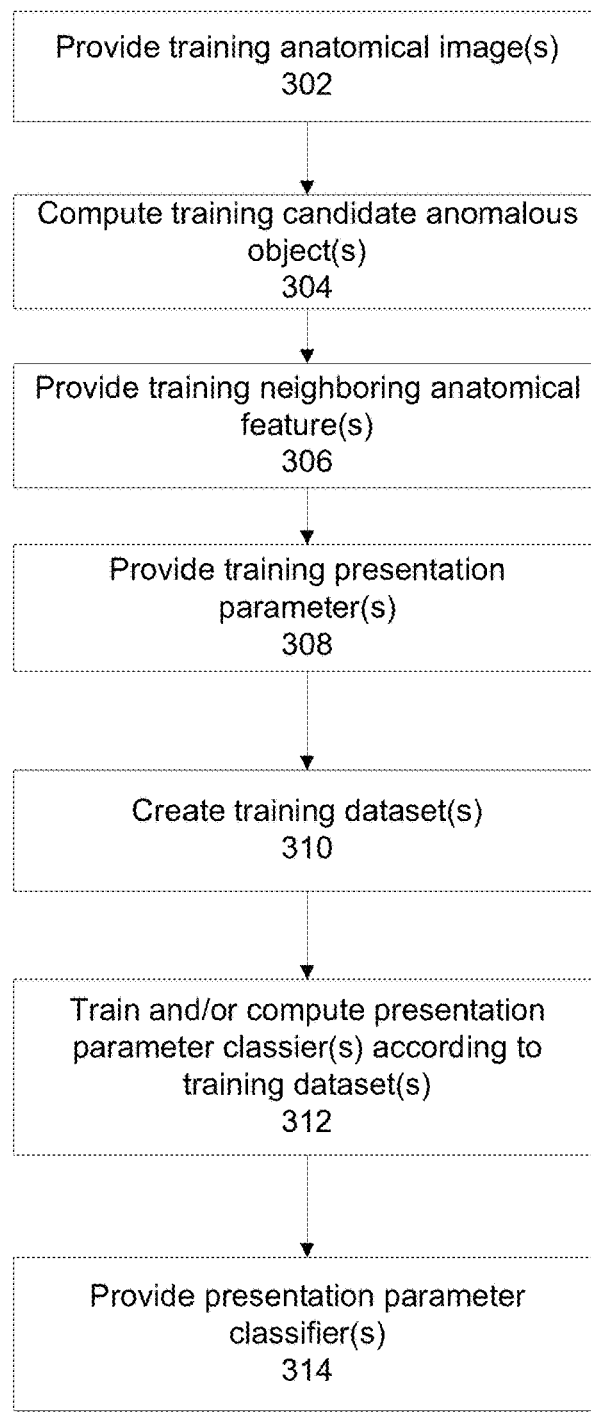
FIG. 3 is a flowchart of a method for training and/or computing a presentation parameter classifier for computing presentation parameter(s) for generating an adapted presentation of candidate anomalous object(s) automatically detected from anatomical imaging data of a target individual, in accordance with some embodiments of the present invention.

Reference is also made to FIG. 2, which is a block diagram of components of a system 200 for automatically generating an adapted presentation of candidate anomalous object(s) automatically detected from anatomical imaging data of a target individual, in accordance with some embodiments of the present invention. Reference is also made to FIG. 3, which is a flowchart of a method for training and/or computing a presentation parameter classifier for computing presentation parameter(s) for generating an adapted presentation of candidate anomalous object(s) automatically detected from anatomical imaging data of a target individual, in accordance with some embodiments of the present invention. System 200 may implement the acts of the method described with reference to FIG. 1 and/or FIG. 3, optionally by a hardware processor(s) 202 of a computing device 204 executing code instructions stored in a memory 206.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that may be implemented as an add-on to a radiology workstation and/or other devices for generating the adapted presentation of the candidate anomalous objects.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser.

Is it noted that the training of the detection classifier and/or the presentation parameter classified, analysis of the anatomical medical images to identify candidate anomalous object(s), computation of the presentation parameter, and/or computation of the adapted presentation according to the presentation parameters, may be implemented by the same computing device 204, and/or by different computing devices 204, for example, one computing device 204 trains the classifiers, and transmit the trained classifiers to a server device 204 which computes the presentation parameters and/or generates the adapted presentation.

Computing device 204 receives anatomical images captured by an anatomical imaging device(s) 212. Exemplary anatomical imaging device(s) 212 include: an ultrasound machine (e.g., 2D, 3D, 4D), an x-ray machine, a magnetic resonance imaging (MRI) device, a computed tomography (CT) machine, and a positron emission tomography (PET) machine. Anatomical images captured by imaging machine 212 may be stored in an image repository 214, for example, a storage server, a computing cloud, virtual memory, and a hard disk. Training images 216A may be created based on the captured anatomical images, as described herein. Alternatively or additionally, training presentation parameters 216B may be selected for the captured anatomical images, as described herein.

Training images 216A are used to train the detection classifier, as described herein. Training presentation parameters 216B are used to train the presentation parameter classifier, as described herein. It is noted that training images 216A and/or training presentation parameters 216B may be stored by a server 218, accessibly by computing device 204 over network 210, for example, a publicly available training dataset, and/or a customized training dataset created for training the detection classifier and/or for training the presentation parameter classifier, as described herein.

Anatomical images captured by imaging machine(s) 212 depict anatomical features and/or anatomical structures within a body portion of the target patient, for example, a chest CT, an abdominal CT, an MRI of the chest and/or abdomen, an x-ray of a limb (e.g., arm, leg), and a head CT.

Computing device 204 may receive the training images 216A and/or training parameters 216B and/or anatomical images from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 206 stores code instructions for implementing trained detection classifier 222A and/or trained presentation parameter classifier(s) 222B. Memory 206 stores image processing code 206A that implements one or more acts and/or features of the method described with reference to FIG. 1, and/or training code 206B that executes one or more acts of the method described with reference to FIG. 3.

Computing device 204 may include a data storage device 222 for storing data, for example, trained detection classifier 222A and/or trained presentation parameter classifier(s) 222B, and/or training images 216A and/or training parameters 216B. Data storage device 222 may be implemented as, for example, a memory, a local hard-drive, a removable storage device, an optical disk, a storage device, and/or as a remote server and/or computing cloud (e.g., accessed over network 210). It is noted that trained detection classifier 222A and/or trained presentation parameter classifier(s) 222B, and/or training images 216A and/or training parameters 216B may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216A and/or download training presentation parameters 216B and/or to download an updated version of image processing code 206A, training code 206B, and/or the trained detection classifier 222A and/or trained presentation parameter classifier(s) 222B.

Computing device 204 may communicate using network 210 (or another communication channel, such as through a direct link (e.g., cable, wireless) and/or indirect link (e.g., via an intermediary computing device such as a server, and/or via a storage device) to implement different possible architectures based on the components of system 200, with one or more of the following:

Client terminal(s) 208, for example, when computing device 204 acts as a server providing image analysis services (e.g., SaaS) to remote radiology terminals, for analyzing remotely obtained anatomical images.

Server 218, for example, implemented in association with a PACS, which may storage large numbers of anatomical images for analysis, for example, captured by an imaging machine of a radiology clinic.

Anatomical image repository 214 that stores training images 216 and/or anatomical images outputted by imaging device 212.

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 that includes a mechanism designed for a user to enter data (e.g., patient data) and/or view the generated adapted presentation. Exemplary user interfaces 226 include, for example, one or more of, a touchscreen, a display, a stereo display, a virtual reality headset, a device that creates a three dimensional presentation, a keyboard, a mouse, and voice activated software using speakers and microphone.

Referring now back to FIG. 1, at 102, the detection classifier(s) is provided and/or trained.

Multiple detection classifiers may be trained. For example, detection classifier may be trained to process anatomical images acquired by a certain type of anatomical imaging modality, for example, CT, MRI, PET, ultrasound, and x-ray. In another example, detection classifiers may be trained to detect a certain type of anomalous object, for example, to detect solitary pulmonary nodules. In another example, detection classifiers may be trained according to dimensions of the input data, for example, to process 2D images, 3D images, or 4D images. In another example, detection classifiers may be trained according to body portion depicted in the anatomical image, for example, head, chest, abdomen, and limb.

The detection classifier may be selected from multiple available detection classifiers. The selection may be performed manually by the user (e.g., via a user interface, for example, displaying a menu and/or icons of available detection classifiers). The selection may be performed automatically by code that determines the image type according to the imaging modality machine (e.g., based on file type, DICOM metadata, automatic analysis of the image). The selection may be performed automatically by code that determines the type of anatomical objects being searched, for example, according to the clinical indication (e.g., obtained from the electronic medical record of the patient and/or according to the issued imaging order). The automated selection may be, for example, based on an analysis of the image itself, and/or an analysis of metadata of the image, and/or according to data associated with the image series (e.g., obtained from a PACS server, DICOM data, and/or electronic medical record).

The detection classifier may be trained according to a training dataset of training images labeled with identified anomalous objects. The labels may be created by manual annotation of the images, for example, performed by a trained radiologist. Anomalous objects may be tagged, for example, with an indication of the type of respective anomalous object. For example, type of the pulmonary nodule, such as solid, semi-solid, and ground-glass. The type may be stored as metadata and/or tag. Candidate anomalous objects detected by the detection classifier may be considered as true positives when located within a distance from a center of a marked anomalous object included in the training images, where the distance is set according to a dimension of the reference marked anomalous object (e.g., radius of a reference pulmonary nodule).

The detection classifier outputs a location of the detected candidate anomalous object, for example, coordinates of pixel elements (e.g., pixels, voxels) corresponding to the detected candidate anomalous objects, and/or a classification tag assigned to pixel elements of the anatomical image that are associated with the detected candidate anomalous objects. As used herein, the term location may refer to spatial locations, optionally with reference to the anatomical image.

The detection classifier may output the indication of neighboring anatomical features, for example, as described with reference to act 110.

Figure 4:
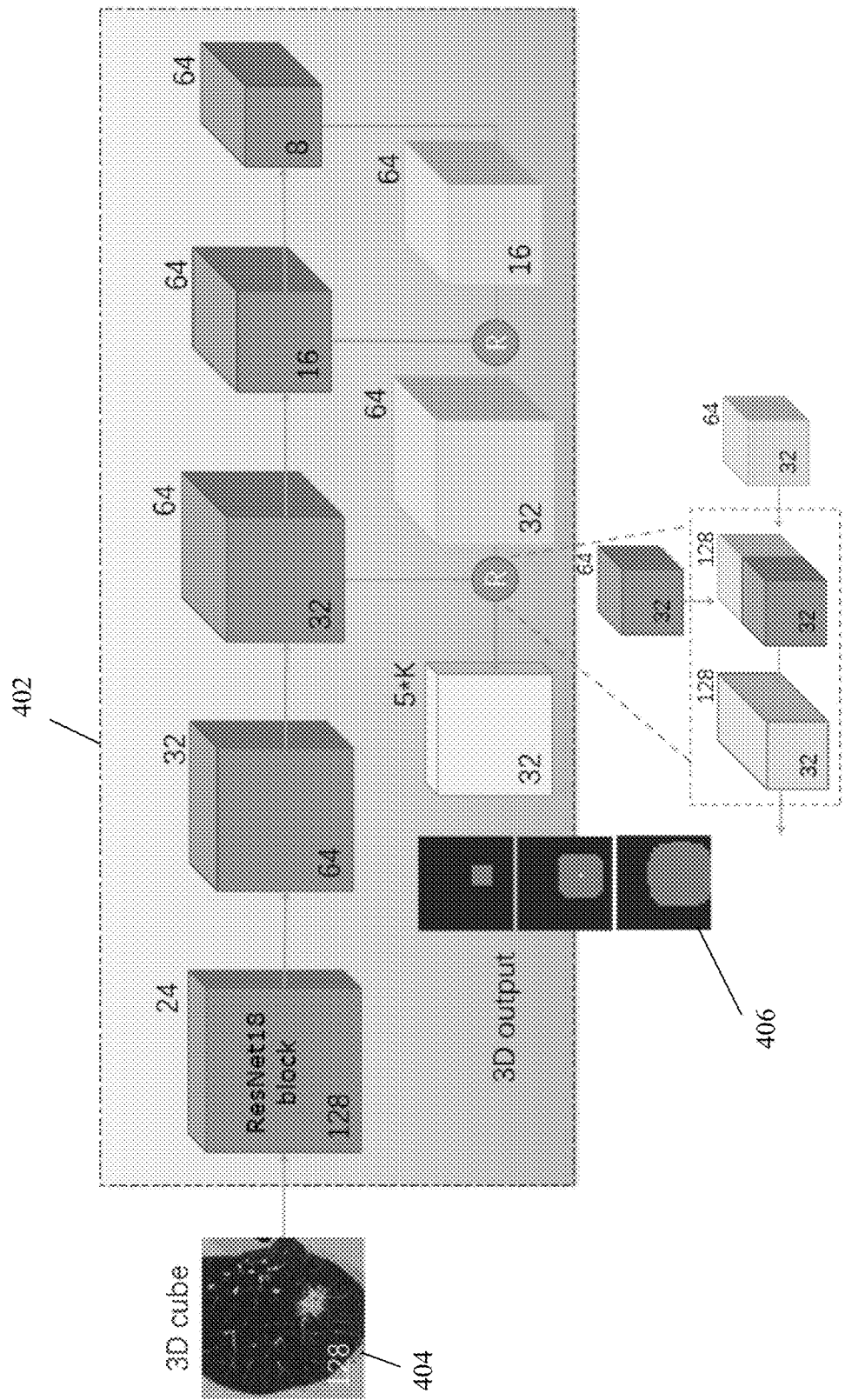
FIG. 4 is a schematic of an exemplary detection classifier that receives a 3D anatomical image and outputs segmented detected anomalous object(s), in accordance with some embodiments of the present invention.

Reference is now made to FIG. 4, which is a schematic of an exemplary detection classifier 402 that receives a 3D anatomical image 404 and outputs segmented detected anomalous object(s) 406, in accordance with some embodiments of the present invention. Detection classifier 402 is implemented as a three dimensional convolutional neural network (CNN), based on region-based fully convolutional network (R-FCN), which is a semantic segmentation based detection architecture. Exemplary detection classifier 402 based on R-FCN is implemented using 3D ResNet18 blocks with U-NET as the FCN model. The training of classifier 402 may be based on Faster-RCNN policy that uses multiple anchors to train the network.

It is noted that detection classifier may be implemented using other methods, for example, other neural network architectures designed according to the type and/or features of the target anomalous objects.

Referring now back to FIG. 1, at 104, a presentation parameter classifier(s) is trained and/or provided.

The presentation parameter classifier may be trained and/or selected according to the detection classifier, for example, according to the same type of anatomical images acquired by the same type of anatomical imaging modality that were fed into the detection classifier, according to the type of anomalous object detected by the detection classifier, according to the same dimension of the input image fed into the detection classifier, and according to the same body portion depicted in the anatomical image fed into the classifier.

The presentation parameter classifier may be linked to the detection classifier, such that selection of the presentation parameter classifier is performed according to the selected detection classifier.

The presentation parameter classifier and the detection classifier may be implemented as two independent classifiers that are cascaded, where output of the detection classifier is fed into the presentation parameter classifier. Alternatively, the presentation parameter classifier and the detection classifier are implemented as a single and/or common classifier, where the single and/or common classifier outputs the presentation parameters and an indication of the detected candidate anomalous objects in response an anatomical image fed into single and/or common classifier.

The presentation parameter classifier may be trained according to a training dataset of training images labeled with identified anomalous objects, and associated presentation. The presentation may be created by a trained radiologist, for example, according to best practices for visualizing the candidate anomalous objects for determining a diagnosis thereof (e.g., an actual anomaly or not). The presentation parameters, as described herein, may be automatically and/or manually extracted from the selected presentation. In another example, the presentation parameter classifier may be defined according to a set of rules and/or code instructions that may be manually and/or automatically defined, for example, based on best radiology practices and/or practical selection process for best visualization of the candidate anomalous objects.

Exemplary architectural implementation of the parameter classifier include one or more of (e.g., arranged as cascade classifiers, parallel classifiers, and/or a combined architecture): multiple Instance Learning (MIL) based methods, one or more neural networks which may include an individual neural network and/or an architecture of multiple neural networks (e.g., convolutional neural network (CNN), fully connected neural network), deep learning based methods, support vector machine (SVM), sets of rules, logistic regression, and k-nearest neighbor, and decision trees.

At 106, anatomical imaging data denoting one or more anatomical images of the target individual are provided. The anatomical imaging data is acquired by an anatomical imaging device, for example, CT, MRI, PET, US, and/or x-ray.

The provided anatomical image may sometimes be referred to herein as the target anatomical image.

The anatomical imaging data may be provided as a 3D volume (e.g., MRI) as a set of 2D slices of the 3D volume (e.g., CT), and/or as single 2D images (e.g., acquired by x-ray and/or US machines).

Optionally, the anatomical imaging data is provided in its raw form, optionally at its original acquired resolution, without necessarily performing additional pre-processing, for example, without performing normalization, without performing interpolation, and/or without performing resizing.

The images may be obtained, for example, from a PACS server, an EMR server, from the anatomical imaging device, and/or from a storage device (e.g., portable storage medium, storage server).

At 108, the anatomical imaging data is provided as input for the detection classifier. The detection classifier outputs an indication of detected candidate anomalous object(s), and an associated location (e.g., spatial location) of the detected candidate anomalous object(s) within the anatomical image. For example, the detection classifier may output a segmentation indicative of the detected candidate anomalous object(s). The segmentation may be, for example, an outline of the detected candidate anomalous object(s), and/or tagging of pixel elements (e.g., pixels, voxels) of the anatomical image associated with the detected candidate anomalous object(s), and/or a coloration of pixel elements (e.g., pixels, voxels) of the anatomical image associated with the detected candidate anomalous object(s). The segmentation inherently includes the location of the detected candidate anomalous object(s). Alternatively or additionally, the detection classifier may output an indication for the anatomical image indicative of whether candidate anomalous object(s) were found (or not found), and output coordinates of pixels of the candidate anomalous object(s).

Optionally, the detection classifier outputs, for each detected candidate anomalous object, an associated probability value (or range of values) indicative of estimate likelihood of the respective candidate anomalous object denoting an actual anomaly. For example, a probably value of 65% indicates that the detected anomalous object has a 65% probability of being an actual anomaly, and 35% probability of not being an anomaly.

Optionally, a sub-set of the candidate anomalous objects are selected according to a target requirement of the computed associated probability values. The target requirement may be a range denoting statistical uncertainty for automatically designating the candidate anomalous objects as actual anomalies. Candidate anomalous objects meeting the target requirements, which represent anomalous objects requiring further analysis, are further processed as described herein. The further processing includes computation of the presentation parameter(s) for each member of the selected subset of the candidate anomalous objects. The adapted presentation is generated for each member of the selected subset of candidate anomalous objects according to corresponding presentation parameter, as described herein.

Optionally, the target requirement (e.g., range) may include a lower limit (e.g., a lower threshold) denoting statistically insignificant likelihood of the respective candidate anomalous object being designated as an actual anomaly. Candidate anomalous objects having probabilities values below the lower threshold denote objects that are unlikely to be designated as actual anomalies. The target requirement (e.g., range) may include an upper limit (e.g., upper threshold) denoting statistically significant likelihood of the respective candidate anomalous object being designated as an actual anomaly. Candidate anomalous objects having probabilities values above the upper threshold denote objects that are likely to be designated as actual anomalies. Candidate anomalous objects having probability values falling within the target requirement (e., range) denote candidate anomalous objects for which the probability value is a statistically uncertainty.

Automated methods may not be able to accurately classify candidate anomalous objects having probability values falling within the target requirement (e., range) into anomalies or not anomalies. Candidate anomalous objects having probability values falling within the target requirement (e., range) require manual intervention by an expert to determine whether each is an anomaly or not. Candidate anomalous objects having probability values falling within the target requirement (e., range) are further processed as described herein, for computation of the presentation parameters and generation of the adapted presentation. The expert user may manually inspect the adapted presentation to determine whether the candidate anomaly objects are actual anomalies or not.

The target requirement, such as range and/or upper threshold and/or lower threshold may be selected, for example, manually by the user, automatically by code, and/or obtained from a data storage device storing predefined values. The target requirement may be selected according to type of anomalous object. For example, when searching for pulmonary nodules which have a risk of malignancy, the thresholds may be set accordingly to avoid missing malignancies, at the potential cost of performing additional biopsies. Exemplary thresholds include: the lower threshold selected from the range 50-70%, or about 60%-80%, or about 50%-80%, and the upper threshold is selected from the range 90-100%, or 80%-100%, or 75%-95%, or 90%-95%, or other values.

At 110, one or more anatomical features indicative of neighboring anatomical features located in proximity to the candidate anomalous objects may be detected.

Exemplary neighboring anatomical features include, for example: organ(s) within which the respective candidate anomalous object is located, tissue type within which the respective candidate anomalous object is located, and normal predefined anatomical landmark in proximity to the respective candidate anomalous object.

Candidate neighboring anatomical features may be according to the type of the candidate anomalous object(s). For example, for pulmonary nodules (i.e., candidate anomalous object(s), candidate neighboring anatomical features may include: chest wall, lung tissue, blood vessels, and airways.

Optionally, the anatomical feature(s) indicative of neighboring anatomical features located in proximity to each respective candidate anomalous objects are computed by a segmentation classifier. The segmentation classifier may segment a patch of the anatomical imaging data that includes the respective candidate anomalous object. The patch may be selected according to the computed location of the candidate anomalous objects. The patch may be selected according to the portion of the anatomical image selected for generation of the adapted presentation. Alternatively or additionally, the portion used for generation of the adapted presentation may be defined according to the selected patch. The segmentation classifier may be implemented as, for example, a distinct segmentation classifier trained, for example, according to type of candidate anomalous object(s) and/or types of expected neighboring anatomical features. For example, for a detected candidate pulmonary nodule, the segmentation classifier may segment the chest wall, blood vessels (e.g., above a threshold size) and/or airways (e.g., above a threshold size).

Alternatively or additionally, the anatomical feature(s) indicative of neighboring anatomical features located in proximity to each respective candidate anomalous objects are computed by the detection classifier(s), optionally processed in parallel and/or simultaneously with the detection of the candidate anomalous object(s). Alternatively or additionally, detection classifier(s) trained to detect the neighboring anatomical features compute the neighboring anatomical features.

Exemplary architectures of segmentation classifiers include: one or more neural networks which may include an individual neural network and/or an architecture of multiple neural networks (e.g., convolutional neural network (CNN), fully connected neural network), deep learning based methods, support vector machine (SVM), sets of rules, logistic regression, and k-nearest neighbor, and decision trees.

Optionally, the distance and/or orientation (e.g., angles in 3D space, vector notation) of the detected neighboring anatomical feature(s) with reference to each candidate anomalous object is computed. For example, the distance and/or orientation from the pulmonary nodule to the closest point on the segmented chest wall is computed.

At 112, reference anatomical images (also referred to herein as similar anatomical images) that are similar to the anatomical image being processed may be searched and/or obtained, for example, from a reference dataset storing pre-analyzed anatomical images, for example, in a PACS server, and/or electronic medical record. The similar anatomical image(s) have been previously viewed by an expert user (e.g., radiologist) and assigned a diagnosis based on visual observation. Generated presentations and/or presentation parameters used for viewing the anatomical image for making the diagnosis may be stored in the dataset. The generated presentations and/or presentation parameters may be computed as described herein.

Optionally, the reference anatomical imaging data (i.e., the reference anatomical images) includes one or more reference anomalous objects correlated to the detected candidate anomalous object. The correlation may be, for example, according to one or more of: similar or same type of anomalous object between the detected candidate anomalous object and the reference anomalous object, similar or same size (e.g., within a tolerance requirement such as range) of the detected candidate anomalous object and the reference anomalous object, similar or same location (e.g., relative to neighbor anatomical features and/or within a tolerance requirement such as range) of the detected candidate anomalous object and the reference anomalous object, for a similar clinical indication (e.g., lung cancer screen), for a similar or same anatomical imaging device (e.g., CT, MRI), for a similar patient (e.g., similar demographic profile), and/or for a similar image acquisition protocol (e.g., low dose chest CT). For example, for a chest CT of a target patient including detected candidate pulmonary nodule located within a certain lobe of a certain lung at a certain distance and/or orientation away from the chest wall, an reference chest CT of a reference patient including a diagnosed pulmonary nodule located at a corresponding similar location (within the tolerance requirement such as range) is found.

The presentation parameter(s) described herein of the anatomical image with candidate anomalous object(s) may be selected according to the obtained reference anatomical image(s). The presentation parameter(s) of the sub-set of the anatomical imaging data including the candidate anomalous object(s) may be obtained according to corresponding stored presentation parameters associated with the reference anatomical imaging data. For example, the same (or similar) presentation parameters used for the reference anatomical image (for which a diagnosis was made of the correlated anomalous object(s) are selected for the current anatomical image.

Optionally, the adapted presentation of the sub-set of the anatomical imaging data (generated as described herein) is presented in association with a presentation of the reference anatomical image. For example, the presentations of sub-set of the anatomical image and the reference anatomical image are generated using similar (or same) presentation parameters, and displayed side by side on a display. The user may view the presented reference anatomical image as an aid in interpreting the candidate anomalous objects of the anatomical image.

The presentation of the sub-set of the anatomical imaging data including the candidate anomalous object(s) may be generated according to the presentation parameters of the reference anatomical image(s), for example, by using the same (or an adaption thereof) of the presentation parameters used for the reference anatomical image(s) for interpretation of the abnormal findings thereof (e.g., stored in association with the reference anatomical image). Alternatively or additionally, the presentation of the reference anatomical image is generated using the presentation parameter(s) computed for of the sub-set of the anatomical imaging data including the candidate anomalous object, as described herein. Using similar (or same) presentation parameters creates similar presentations for the reference and current anatomical images, which may improve the ability of the user (e.g., radiologist) to interpret the candidate anatomical objects, by comparing to the known interpreted reference objects of the reference image.

At 114, a presentation parameter classifier computes one or more presentation parameter for adapting a presentation of a sub-set of the anatomical imaging data including the candidate anomalous object(s). The presentation parameter classifier computes the presentation parameters(s) in response to input of at least the location of the candidate anomalous object(s) and neighboring anatomical feature(s) indicative of anatomical features located in proximity to the candidate anomalous object.

Exemplary architectural implementation of the presentation parameter classifier include one or more of (e.g., arranged as cascade classifiers, parallel classifiers, and/or a combined architecture): one or more neural networks which may include an individual neural network and/or an architecture of multiple neural networks (e.g., convolutional neural network (CNN), fully connected neural network), deep learning based methods, support vector machine (SVM), sets of rules, logistic regression, and k-nearest neighbor, and decision trees.

The presentation parameter(s) is selected for improving visual inspection of the candidate anomalous object(s) relative to neighboring anatomical features. For example, for improving the accuracy of a user in manually inspecting the generated presentation for classification and/or interpretation of the candidate anomalous object as an anomaly. For example, the presentation parameters are selected to removing neighboring anatomical structures so that an unobstructed view of the candidate anomalous object(s) is created, and/or orienting the anatomical image so that a distance between candidate anomalous object(s) and neighboring anatomical features is apparent, or to improve the ability to determine whether the candidate anomalous object(s) is touching the neighboring anatomical feature(s).

Optionally, a unique set of presentation parameters is computed independently for each respective candidate anomalous object. The unique set of presentation parameters is computed according to respective corresponding sub-set of the anatomical imaging data, according to the location of the respective candidate anomalous object and neighboring anatomical features. For example, for multiple pulmonary nodules detected at different locations in the lungs of a target individual, the unique set of presentation parameters is computed for each pulmonary nodule, according to the location of each respective pulmonary nodule within the lungs (e.g., apex, based, left or right lung, lobe) and neighboring anatomical structures (e.g., distance to chest wall). Each unique set of parameters may be computed according to features that are unique to the respective candidate anomalous object. A unique adapted presentation may be generated independently for each respective candidate anomalous object according to respective corresponding unique set of presentation parameters.

Some exemplary presentation parameters are now discussed. Values for one or more of the following presentation parameters may be automatically computed by the presentation parameter classifier:

Dimensions of the sub-set of the anatomical imaging data including the candidate anomalous object(s). The dimensions may be selected for including in the sub-set of the anatomical image, the external boundaries of a target neighbor anatomical feature(s) and at least a portion of anatomical features located in proximity to the candidate anomalous object(s). For example, the dimensions for pulmonary nodule(s) may be selected to include at least a portion of the closest chest wall.

A scale factor for enlarging the sub-set of the anatomical imaging data including the candidate anomalous object(s). The scale factor may be selected according to a target neighboring anatomical feature(s). The scale factor may be inversely correlated to a distance to the target neighboring anatomical feature(s). A relatively larger scale factor is selected for a relatively smaller distance. For example, the smaller the distance between a pulmonary nodule and a chest wall, the larger the scale factor. The larger scale factor may enable the user to determine whether the pulmonary nodule (or other candidate anomalous object(s)) is contacting the chest wall (or other target anatomical feature) or not.

A rotation angle of the sub-set of the anatomical imaging data including the candidate anomalous object(s). The rotation angle is for rotating the sub-set of the anatomical image to defined viewing angle(s). The rotation angle may be selected according to the neighboring anatomical feature(s). The viewing angle may be selected according to one or more of: removing or reducing obstructions from the anatomical features located in proximity to the candidate anomalous object, position anatomical features located in proximity to the candidate anomalous object at a predefined reference orientation, and depict selected anatomical features of the candidate anomalous object(s). For example, the rotation angle may be selected to position the portion of the chest wall closest to the pulmonary nodule face on, such that the chest wall appears next to the pulmonary nodule rather than in front or behind the pulmonary nodule. Such orientation of the chest wall allows the user to more accurately determine whether the pulmonary nodule is contacting the chest wall or not.

A value of a CT window (or other imaging modality). The CT window (or other imaging modality) may be selected according to the neighboring anatomical feature(s) in proximity to the candidate anomalous object(s). For example, a lung window is selected when the candidate anomalous object(s) is located within the lung.

Based on a segmentation of the candidate anomalous object and/or segmentation of neighboring anatomical features located in proximity to the candidate anomalous object(s). Segmentation may be performed, for example, by a segmentation classifier (and/or other coded implementation) as described herein. Exemplary presentation parameters selected based on segmentation of the candidate anomalous object and/or segmentation of neighboring anatomical features include: removing neighboring anatomical features located externally to the boundaries of the segmented candidate anomalous object(s), coloring the segmented candidate anomalous object(s) with color(s), highlighting the segmented candidate anomalous object(s), extracting the segmented candidate anomalous object(s), and skeletonization of the segmented candidate anomalous object(s).

At 116, an adapted presentation of the sub-set of the anatomical imaging data including candidate anomalous object(s) is generated according to the computed presentation parameter(s). The presentation may be generated, for example, by a rendering engine with multiple options.

The presentation may be displayed, for example, on a 2D display, on a 3D display, on a virtual reality display (e.g., virtual reality glasses). The presentation may be, for example, a still 2D image, a 3D image, and a video.

Optionally, when the presentation parameter(s) include multiple rotation angles, the adapted presentation may include a video created by rotation of the sub-set of the anatomical imaging according to the rotation angles.

The presentation may be provided, for example, displayed on a display, stored in a data storage device, and/or transmitted to a remote computing device (e.g., server, administrative client terminal).

It is noted that the presentation may be generated independently of the parameters. The type of presentation may be selected, for example, based on user preference and/or according to available hardware. For example, the presentation parameters may be stored in association with the anatomical image. The presentation parameters may be provided to a client terminal. The client terminal may automatically generate the presentation according to the presentation parameter and optionally according to locally available hardware and/or user selection. The same set of parameters may result in different generated adapted presentations. For example, a first user using a 2D display may view the presentation generated from the presentation parameters, while a second user using 3D virtual reality headset may view a different presentation generated from the same presentation parameters.

Referring now back to FIG. 3, at 302, training anatomical images are provided for each of multiple sample individuals. Different types of anatomical images may be provided. Anatomical images may be provided, for example, as described with reference to act 106 of FIG. 1.

At 304, for each respective training anatomical imaging data, an indication of training candidate anomalous object(s) and associated location thereof are computed by a detection classifier, for example, as described with reference to act 108 of FIG. 1. Optionally, the training candidate anomalous object(s) are not determined manually (e.g., by a user manually delineating the borders of the training candidate anomalous object(s)), but are determined by the detection classifier.

One or more types of detection classifiers may be used, for example, as described with reference to act 108 of FIG. 1.

At 306, training neighboring anatomical feature(s) indicative of training neighboring anatomical features located in proximity to each training candidate anomalous object of each anatomical image of each sample individual may be provided. The training neighboring anatomical feature(s) may be computed, for example, by the segmentation classifier described herein. The training neighboring anatomical feature(s) may be computed, for example, as described with reference to act 110 of FIG. 1.

At 308, training presentation parameter(s) are provided for each respective training anatomical imaging data, optionally for each training candidate anomalous object(s). The training presentation parameter(s) are selected for adapting a presentation of a sub-set of the anatomical imaging data including the respective training candidate anomalous object according to associated location thereof and neighboring anatomical feature(s).

Training presentation parameter(s) may be obtained, for example, manually provided by a user (e.g., expert radiologist), and/or automatically extracted from a presentation manually created by the user. For example, the user rotates the anatomical image to a certain viewing angle, and parameters associated with the presentation are stored.

At 310, one or more training datasets are created for training one or more presentation parameter classifiers. Each training dataset includes training candidate anomalous object(s), an associated location of the respective training candidate anomalous object(s), optionally neighboring anatomical feature(s) indicative of anatomical features located in proximity to the respective training candidate anomalous object, and training presentation parameter(s).

At 312, one or more presentation parameter classifiers are trained and/or computed according to the training dataset.

Each presentation parameter classifier is trained for computing presentation parameter(s) for a target anatomical imaging data of a target individual when an indication of candidate anomalous object(s) and associated location thereof, and optionally neighboring anatomical feature(s) indicative of anatomical features located in proximity to the respective training candidate anomalous object, computed for the target anatomical imaging data, are provided as input into the presentation parameter classifier.

The process of training each presentation parameter classifier is according to the architectural implementation and/or type of the respective presentation parameter classifier.

At 314, the trained and/or computed presentation parameter classifier(s) are provided. The trained presentation parameter classifier(s) may be locally stored by the computing device, and/or forwarded to the computing device when the training is performed by another device.

Figure 5:
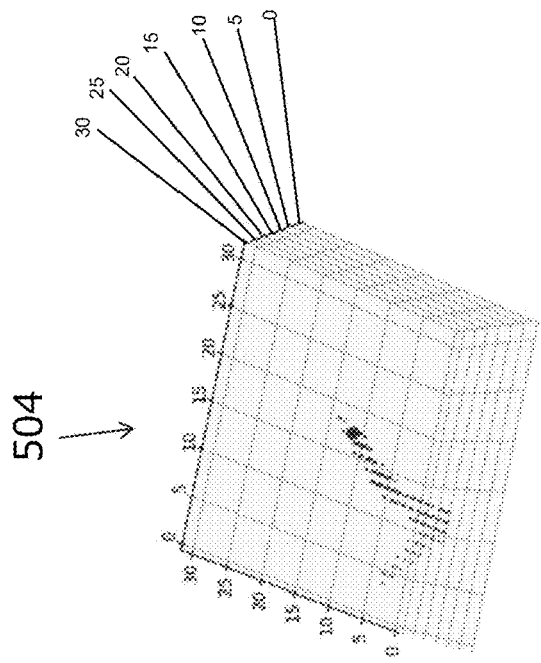
FIG. 5 is a schematic depicting some examples of automatically generated presentations of at least candidate anomalous objects based on selected presentation parameters, in accordance with some embodiments of the present invention.
Figure 5:
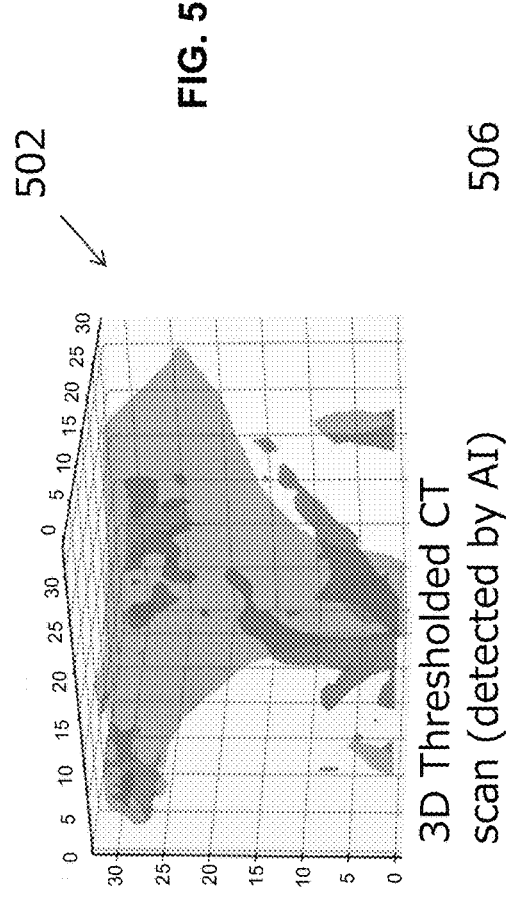
Figure 5:
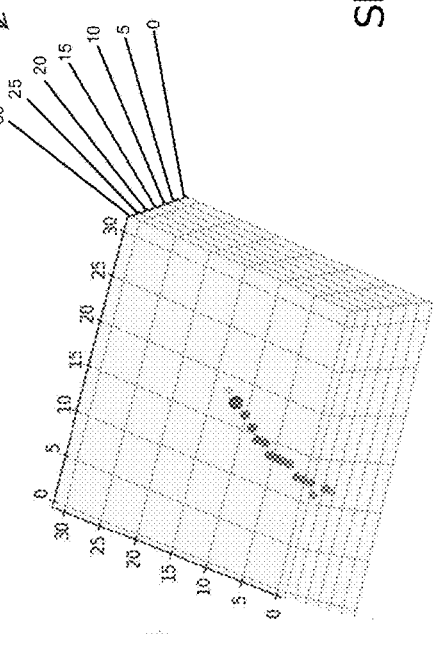

Reference is now made to FIG. 5, which is a schematic depicting some examples of automatically generated presentations of at least candidate anomalous objects based on selected presentation parameters, in accordance with some embodiments of the present invention. A 3D CT scan is obtained and processed to detect candidate anomalous object(s), as described herein. Presentation parameters are selected according to the candidate anomalous objects, as described herein. Presentation 502 is generated based on presentation parameters for thresholding of the 3D CT scan.

Presentation 504 is generated based on presentation parameters for segmenting a single candidate object from the 3D scan, and rotating the segmented candidate object to a target viewing angle. Presentation 506 is generated based on presentation parameters for skeletonizing the single candidate object.

Figure 6:
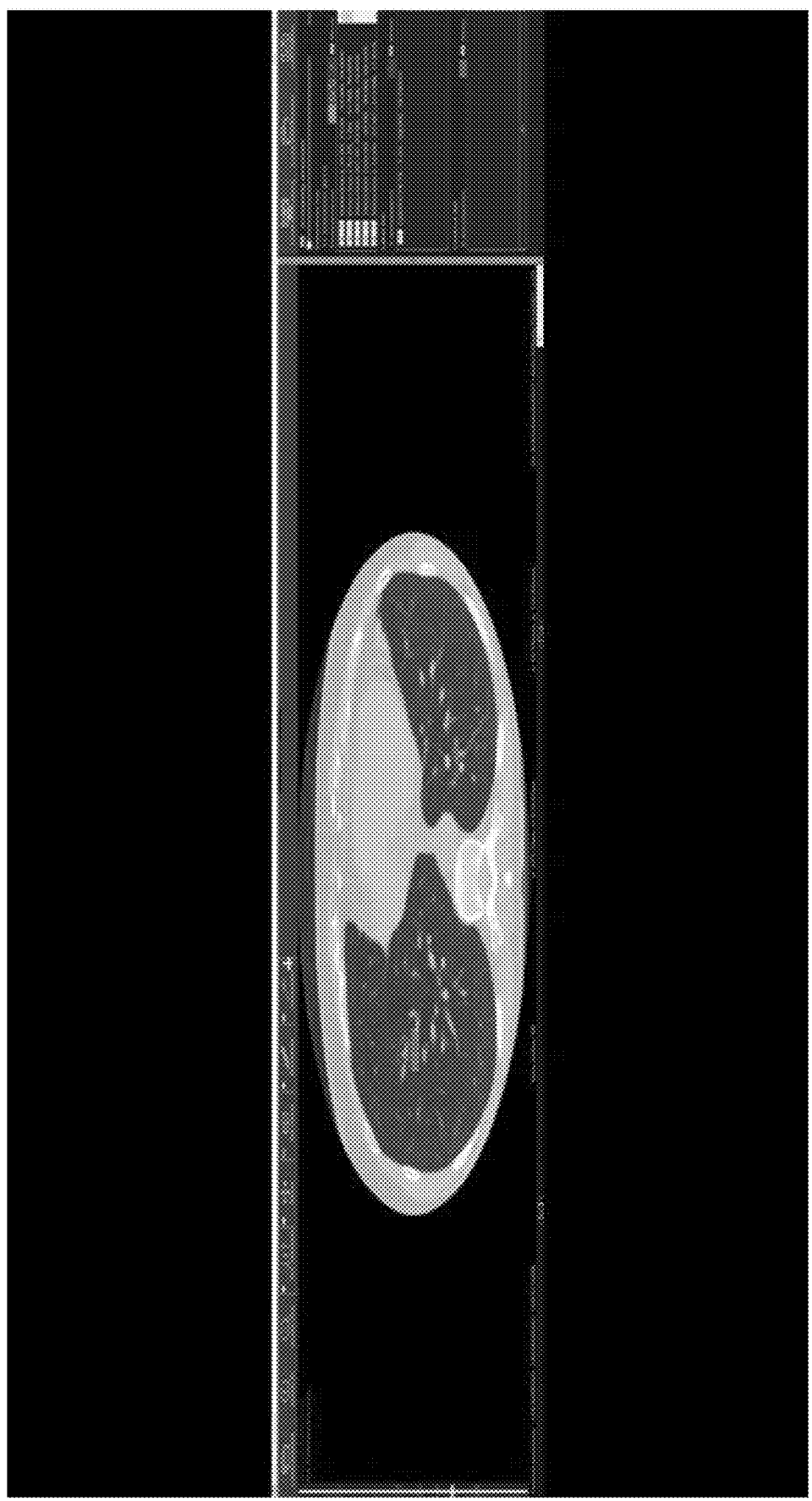
FIG. 6 is a schematic depicting another example of an automatically generated presentation of at least candidate anomalous objects based on selected presentation parameters, in accordance with some embodiments of the present invention.

Reference is now made to FIG. 6, which is a schematic depicting another example of an automatically generated presentation of at least candidate anomalous objects based on selected presentation parameters, in accordance with some embodiments of the present invention. A 3D CT scan is obtained and processed to detect candidate anomalous object(s), as described herein. Presentation parameters are selected according to the candidate anomalous objects, as described herein. Presentation 602 is generated based on presentation parameters that include thresholding of the 3D CT scan, and a segmentation of the region of the anatomical image that includes the candidate anomalous object. Presentation 602 is further generated as an animation and/or video, where the region of the anatomical image is rotate through selected viewing angles (e.g., selected by the presentation parameter classifier).

Figure 7:
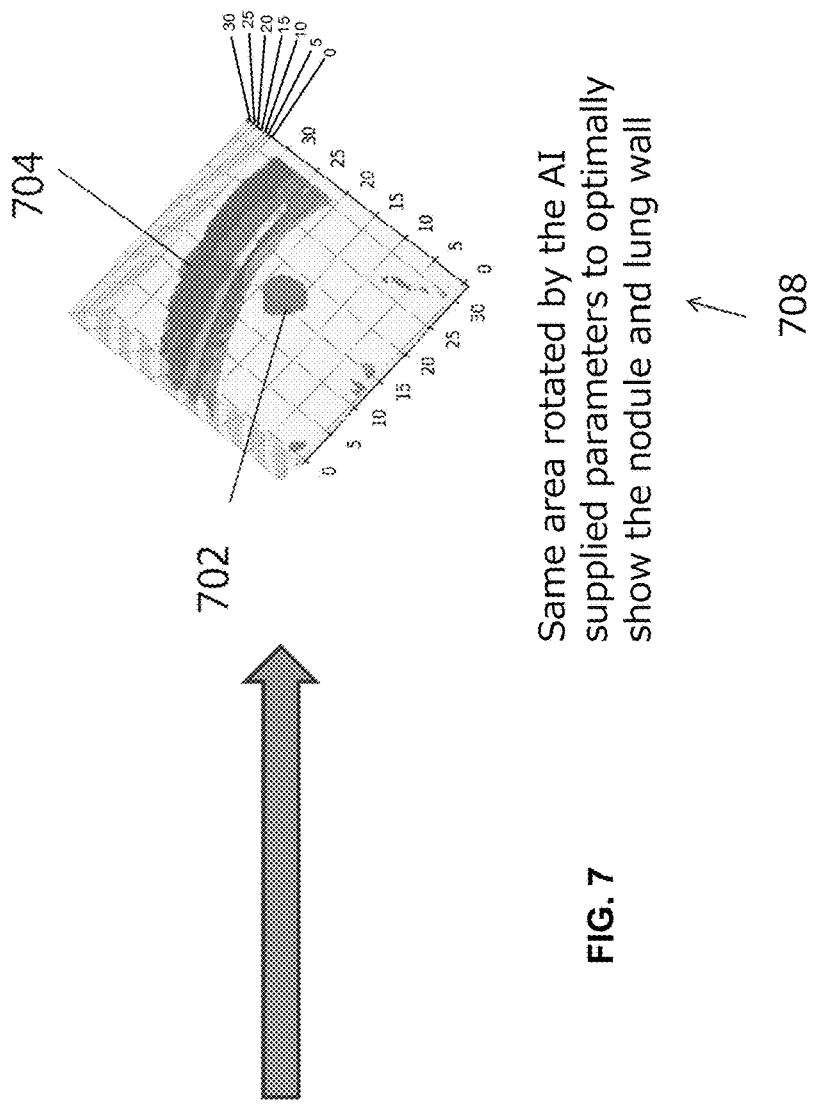
FIG. 7 is a schematic depicting another example of an automatically generated presentation of at least candidate anomalous objects based on selected presentation parameters, in accordance with some embodiments of the present invention.

Reference is now made to FIG. 7, which is a schematic depicting another example of an automatically generated presentation of at least candidate anomalous objects based on selected presentation parameters, in accordance with some embodiments of the present invention. A 3D CT scan is obtained and processed to detect candidate anomalous object(s), as described herein. Presentation parameters are selected according to the candidate anomalous objects, as described herein.

In the present example, a nodule 702 (i.e., candidate anomalous object) is detected in proximity to a lung wall 704 (i.e., neighboring anatomical feature). Image 706 depicts a portion of the CT viewed from the default CT orientation of a supine position. Image 708 is generated based on the selected presentation parameters, which include a rotation for optimally depicting the relationship between nodule 702 and lung wall 704, for example, for determination whether nodule 702 is contacting lung wall 704 or whether nodule 702 is not contacting lung wall 704. The rotation may be selected according to a predefined value denoting optimal orientation. It is noted that in comparison, using image 706 it is difficult to determine whether nodule 702 is contacting lung wall 704.

Figure 8:
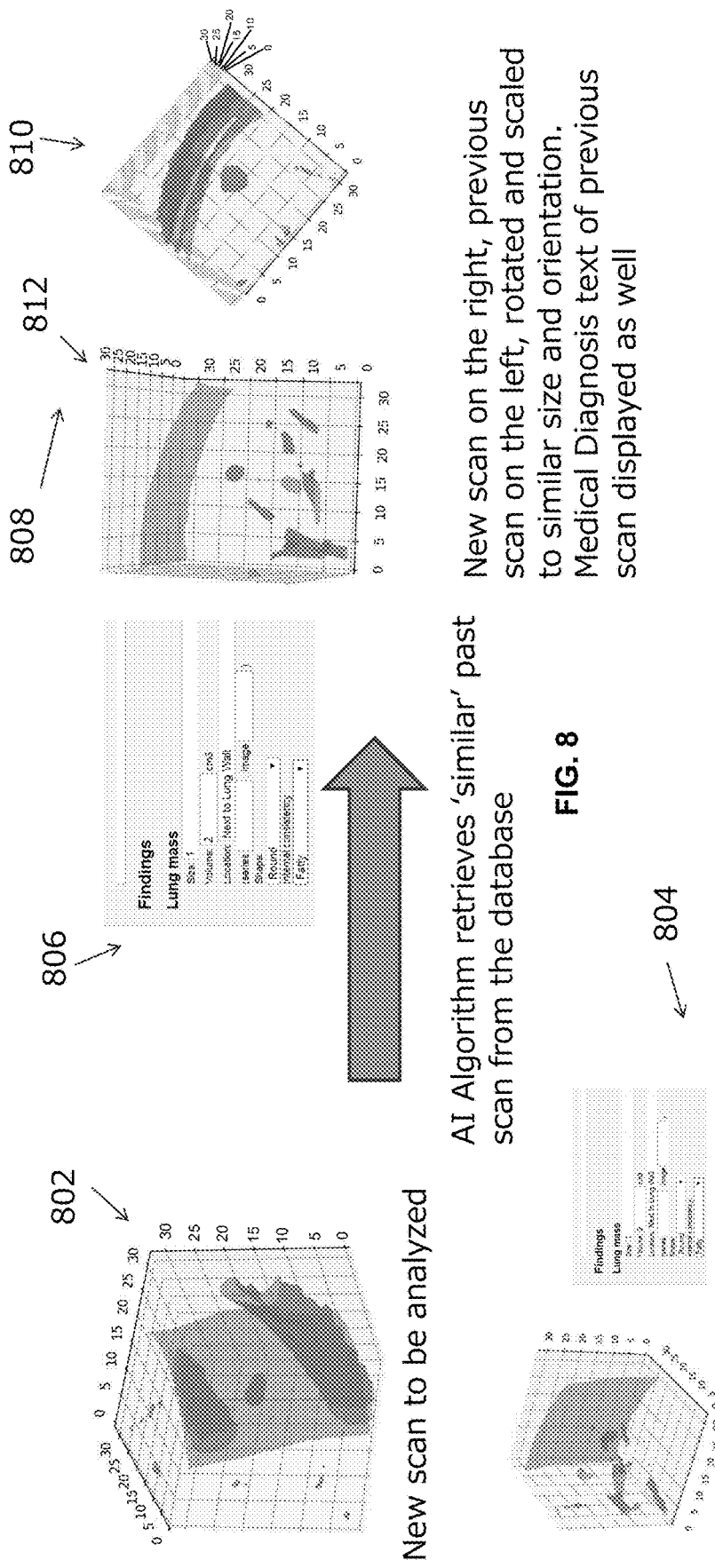
FIG. 8 is a schematic depicting an example of generating a presentation including a reference anatomical image similar to a target anatomical image, in accordance with some embodiments of the present invention.

Reference is now made to FIG. 8, which is a schematic depicting an example of generating a presentation including a reference anatomical image similar to a target anatomical image, in accordance with some embodiments of the present invention. Anatomical image 802 is provided, as described herein. A reference anatomical image dataset stores anatomical images with previously determined anomalous objects 804.

Reference anatomical images may be stored in association with presentation parameters used to generate a presentation for optimal visual inspection of the respective anatomical image (i.e., to make the diagnosis and/or assign a label to the anomalous object). A search 806 is performed to identify reference anatomical images from the dataset that are similar to the target anatomical image, at least having a correlated pulmonary nodule, for example, at a similar location in the lung and/or of a similar size. A presentation 808 is generated, where the presentation parameters are selected according to the presentation parameters of the reference anatomical image. The selected presentation parameters are used to generate the presentation of the target anatomical image 810 and the reference anatomical image 812. Target anatomical image 810 and reference anatomical image 812 are shown side by side using the same (or similar within a threshold) selected presentation parameters.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant classifiers will be developed and the scope of the term classifier is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computed implemented method of automatically generating an adapted presentation of at least one candidate anomalous object detected from anatomical imaging data of a target individual, comprising:
    providing anatomical imaging data of the target individual acquired by an anatomical imaging device;
    analyzing the anatomical imaging data by a detection classifier for detecting at least one candidate anomalous object of the anatomical imaging data and computed associated location thereof;
    computing, by a presentation parameter classifier, at least one presentation parameter for adapting a presentation of a sub-set of the anatomical imaging data including the at least one candidate anomalous object according to at least the location of the candidate anomalous object; and
    generating according to the at least one presentation parameter, an adapted presentation of the sub-set of the anatomical imaging data including the at least one candidate anomalous object;
    wherein the presentation parameter classifier further computes the at least one presentation parameter according to at least one neighboring anatomical feature indicative of one or more anatomical features located in proximity to the candidate anomalous object;
    wherein the at least one presentation parameter comprises dimensions of the sub-set of the anatomical imaging data including the at least one candidate anomalous object, the dimensions selected according to the at least one neighboring anatomical feature;
    wherein the dimensions are selected for including the external boundaries of the at least one neighboring anatomical feature and at least a portion of one or more anatomical features located in proximity to the at least one candidate anomalous object.

2. The method according to claim 1, wherein the at least one anatomical feature indicative of one or more neighboring anatomical features located in proximity to one or more candidate anomalous objects is selected from the group consisting of: organ within which the respective candidate anomalous object is located, tissue type within which the respective candidate anomalous object is located, and normal predefined anatomical landmark in proximity to the respective candidate anomalous object.

3. The method according to claim 1, wherein the at least one anatomical feature indicative of one or more neighboring anatomical features located in proximity to each respective candidate anomalous objects is computed by a segmentation classifier that segments a patch of the anatomical imaging data that includes the respective candidate anomalous object.

4. The method according to claim 1, wherein the at least one presentation parameter is selected for improving visual inspection of the at least one candidate anomalous object relative to one or more neighboring anatomical features, for classification of the at least one candidate anomalous object as an anomaly.

5. The method according to claim 1, wherein a unique set of presentation parameters is computed independently for each respective candidate anomalous object according to respective corresponding sub-set of the anatomical imaging data, and wherein a unique adapted presentation is computed independent for each respective candidate anomalous object according to respective corresponding unique set of presentation parameters.

6. The method of claim 5, wherein the at least one presentation parameter comprises a plurality of rotation angles, and the adapted presentation comprises a video created by rotation of the sub-set of the anatomical imaging according to the plurality of rotation angles.

7. The method of claim 1, further comprising computing a segmentation of the at least one candidate anomalous object, and wherein the at least one presentation parameter is selected according to the segmentation of the at least one candidate anomalous object.

8. The method of claim 7, wherein the at least one presentation parameter is selected from the group consisting of: removing neighboring anatomical features located externally to the boundaries of the segmented at least one candidate anomalous object, coloring the segmented at least one candidate anomalous object with at least one color, highlighting the segmented at least one candidate anomalous object, extracting the segmented at least one candidate anomalous object, and skeletonization of the segmented at least one candidate anomalous object.

9. The method of claim 1, further comprising
    obtaining from a reference dataset, at least one reference anatomical imaging data including at least one reference anomalous object correlated to the detected at least one candidate anomalous object;
    wherein the at least one presentation parameter is selected according to the at least one reference anatomical imaging data; and
    wherein the adapted presentation of the sub-set of the anatomical imaging data is presented in association with a presentation of the at least one reference anatomical image.

10. The method of claim 9, wherein the at least one presentation parameter of the sub-set of the anatomical imaging data including the at least one candidate anomalous object are obtained according to corresponding stored presentation parameters associated with the at least one reference anatomical imaging data.

11. The method of claim 9, wherein the presentation of the at least one reference anatomical image is generated using the at least one presentation parameter computed for of the sub-set of the anatomical imaging data including the at least one candidate anomalous object.

12. The method of claim 1, wherein the imaging data comprises 3D imaging data acquired by a 3D imaging device.

13. The method of claim 12, wherein the 3D imaging device is selected from the group consisting of: computed tomography (CT), magnetic resonance imaging (MRI), positron emission tomography (PET), and ultrasound (US).

14. A computed implemented method of automatically generating an adapted presentation of at least one candidate anomalous object detected from anatomical imaging data of a target individual, comprising:
providing anatomical imaging data of the target individual acquired by an anatomical imaging device;
analyzing the anatomical imaging data by a detection classifier for detecting at least one candidate anomalous object of the anatomical imaging data and computed associated location thereof;
computing, by a presentation parameter classifier, at least one presentation parameter for adapting a presentation of a sub-set of the anatomical imaging data including the at least one candidate anomalous object according to at least the location of the candidate anomalous object; and
generating according to the at least one presentation parameter, an adapted presentation of the sub-set of the anatomical imaging data including the at least one candidate anomalous object;
wherein the presentation parameter classifier further computes the at least one presentation parameter according to at least one neighboring anatomical feature indicative of one or more anatomical features located in proximity to the candidate anomalous object;
wherein the at least one presentation parameter comprises a scale factor for enlarging the sub-set of the anatomical imaging data including the at least one candidate anomalous object, the scale factor is selected according to the at least one neighboring anatomical feature; wherein the scale factor is inversely correlated to a distance to the at least one neighboring anatomical feature, wherein a relatively larger scale factor is selected for a relatively smaller distance.

15. A computed implemented method of automatically generating an adapted presentation of at least one candidate anomalous object detected from anatomical imaging data of a target individual, comprising:
providing anatomical imaging data of the target individual acquired by an anatomical imaging device;
analyzing the anatomical imaging data by a detection classifier for detecting at least one candidate anomalous object of the anatomical imaging data and computed associated location thereof;
computing, by a presentation parameter classifier, at least one presentation parameter for adapting a presentation of a sub-set of the anatomical imaging data including the at least one candidate anomalous object according to at least the location of the candidate anomalous object; and
generating according to the at least one presentation parameter, an adapted presentation of the sub-set of the anatomical imaging data including the at least one candidate anomalous object;
wherein the at least one candidate anomalous object is selected from a plurality of candidate anomalous objects associated with a probability value indicative of estimate likelihood of the respective candidate anomalous object denoting an actual anomaly, and further comprising selecting a subset of anomalous objects from the plurality of candidate anomalous objects; wherein members of the subset having probability values within a range denoting statistical uncertainty for automatically designating the members of the subset as actual anomalies, wherein the at least one presentation parameter is computed for each member of the selected subset, and the adapted presentation is generated for each member of the selected subset according to corresponding at least one presentation parameter.

16. The method according to claim 15, wherein the presentation parameter classifier further computes the at least one presentation parameter according to at least one neighboring anatomical feature indicative of one or more anatomical features located in proximity to the candidate anomalous object.

17. The method according to claim 16, wherein the at least one presentation parameter comprises dimensions of the sub-set of the anatomical imaging data including the at least one candidate anomalous object, the dimensions selected according to the at least one neighboring anatomical feature.

18. The method of claim 16, wherein the at least one presentation parameter comprises a scale factor for enlarging the sub-set of the anatomical imaging data including the at least one candidate anomalous object, the scale factor is selected according to the at least one neighboring anatomical feature.

19. The method of claim 16, wherein the at least one presentation parameter comprises a rotation angle of the sub-set of the anatomical imaging data including the at least one candidate anomalous object to at least one viewing angle selected according to the at least one neighboring anatomical feature.

20. The method of claim 16, wherein the at least one presentation parameter comprises a value of a CT window selected according to the at least one neighboring anatomical feature.

21. The method according to claim 15, wherein the range includes candidate anomalous objects from the plurality of candidate anomalous objects which has probability values above a lower threshold denoting statistically insignificant likelihood of the respective candidate anomalous object being designated as the actual anomaly, and below an upper threshold denoting statistically significant likelihood of the respective candidate anomalous object being designated as the actual anomaly.

22. The method according to claim 21, wherein the lower threshold is selected from the range 50-70%, and the upper threshold is selected from the range 90-100%.

23. A computed implemented method of automatically generating an adapted presentation of at least one candidate anomalous object detected from anatomical imaging data of a target individual, comprising:
providing anatomical imaging data of the target individual acquired by an anatomical imaging device;
analyzing the anatomical imaging data by a detection classifier for detecting at least one candidate anomalous object of the anatomical imaging data and computed associated location thereof;

computing, by a presentation parameter classifier, at least one presentation parameter for adapting a presentation of a sub-set of the anatomical imaging data including the at least one candidate anomalous object according to at least the location of the candidate anomalous object; and generating according to the at least one presentation parameter, an adapted presentation of the sub-set of the anatomical imaging data including the at least one candidate anomalous object;

wherein a unique set of presentation parameters is computed independently for each respective candidate anomalous object according to respective corresponding sub-set of the anatomical imaging data, and wherein a unique adapted presentation is computed independent for each respective candidate anomalous object according to respective corresponding unique set of presentation parameters;

wherein a viewing angle is selected to at least one of: remove or reduce obstructions from one or more anatomical features located in proximity to the candidate anomalous object, position the one or more anatomical features located in proximity to the candidate anomalous object at a predefined reference orientation, and depict selected anatomical features of the at least one candidate anomalous object.

24. A system for automatically generating an adapted presentation of at least one candidate anomalous object detected from anatomical imaging data of a target individual, comprising:
   at least one hardware processor; and
      a non-transitory memory having stored thereon a code for execution by the at least one hardware processor, the code comprising instructions for:
   obtaining anatomical imaging data of the target individual acquired by an anatomical imaging device;
   analyzing the anatomical imaging data by a detection classifier for detecting at least one candidate anomalous object of the anatomical imaging data and computed associated location thereof;
   computing, by a presentation parameter classifier, at least one presentation parameter for adapting a presentation of a sub-set of the anatomical imaging data including the at least one candidate anomalous object according to at least the location of the candidate anomalous object; and
   generating according to the at least one presentation parameter, an adapted presentation of the sub-set of the anatomical imaging data including the at least one candidate anomalous object;
   wherein a unique set of presentation parameters is computed independently for each respective candidate anomalous object according to respective corresponding sub-set of the anatomical imaging data, and wherein a unique adapted presentation is computed independent for each respective candidate anomalous object according to respective corresponding unique set of presentation parameters;
   wherein a viewing angle is selected to at least one of: remove or reduce obstructions from one or more anatomical features located in proximity to the candidate anomalous object, position the one or more anatomical features located in proximity to the candidate anomalous object at a predefined reference orientation, and depict selected anatomical features of the at least one candidate anomalous object.

25. The system of claim 24, further comprising code instructions for:
   obtaining respective training anatomical imaging data for each of a plurality of sample individuals;
   computing by a detection classifier, for each respective training anatomical imaging data, an indication of at least one training candidate anomalous object and associated location thereof;
   obtaining, for each respective training anatomical imaging data, at least one training presentation parameter for adapting a presentation of a sub-set of the anatomical imaging data including the at least one candidate anomalous object according to at least the location of the candidate anomalous object; and
   training the presentation parameter classifier for computing at least one presentation parameter for a target anatomical imaging data of a target individual when an indication of at least one candidate anomalous object and associated location thereof computed for the target anatomical imaging data is provided as input into the presentation parameter classifier.

* * * * *